United States Patent [19]

Klaveness et al.

[11] Patent Number: 5,735,279
[45] Date of Patent: *Apr. 7, 1998

[54] SQUID MAGNETOMETRY USING FERRO-, FERRI- ARE PARAMAGNETIC PARTICLES

[75] Inventors: Jo Klaveness; Thorfinn Ege, both of Oslo, Norway; Scott M. Rocklage, Los Gatos, Calif.

[73] Assignee: Nycomed Imaging AS, Oslo, Norway

[*] Notice: The term of this patent shall not extend beyond the expiration date of Pat. No. 5,384,109.

[21] Appl. No.: 483,168

[22] Filed: Jun. 7, 1995

Related U.S. Application Data

[62] Division of Ser. No. 199,252, filed as PCT/EP92/02254, Sep. 26, 1992, Pat. No. 5,496,534.

[30] Foreign Application Priority Data

Sep. 26, 1991 [GB] United Kingdom ............... 9120508

[51] Int. Cl.⁶ .................................................. A61B 5/055
[52] U.S. Cl. ............... 128/654; 128/653.1; 128/653.4; 424/9.32; 424/9.322; 424/648
[58] Field of Search ................... 128/653.1, 654, 128/653.4; 424/9.1, 9.3, 9.32, 646, 648, 9.322

[56] References Cited

U.S. PATENT DOCUMENTS

| | | | |
|---|---|---|---|
| 5,023,072 | 6/1991 | Cheng | 128/653.4 |
| 5,384,109 | 1/1995 | Klaveness et al. | 128/653.1 |
| 5,496,534 | 3/1996 | Klaveness et al. | 424/9.32 |

Primary Examiner—Ruth S. Smith
Attorney, Agent, or Firm—Bacon & Thomas

[57] ABSTRACT

The invention provides for the use of a physiologically tolerable, particulate, free or matrix-borne, ferromagnetic, ferrimagnetic or paramagnetic material for the manufacture of a diagnostic agent for magnetometric imaging of a human or non-human animal body.

12 Claims, 3 Drawing Sheets

SQUID MAGNETOMETRY USING FERRO-, FERRI- ARE PARAMAGNETIC PARTICLES

CROSS-REFERENCE TO RELATED APPLICATION

This application is a Division of application Ser. No. 08/199,252, filed as PCT/EP92/02254, Sep. 26, 1992, now U.S. Pat. No. 5,496,534.

BACKGROUND OF THE INVENTION

1) Field of the Invention

This invention relates to the use of magnetic substances, in particular ferromagnetic and ferrimagnetic substances, as enhancing agents for diagnostic magnetometery, and in particular as contrast agents in magnetometric imaging, especially using a superconducting quantum interference device magnetometer (a SQUID), preferably in combination with a magnetic resonance imager.

2) Description of the Related Art

In 1963 James Zimmerman, a researcher at Ford Motor Company, observed that when a non-superconducting boundary is present in a superconducting loop a special effect is created. This effect is extremely sensitive to magnetic flux and based on Zimmerman's work the very highly sensitive SQUID magnetometers have been developed and are now available commercially from companies such as Biomagnetic Technologies Inc of San Diego, Calif. and Siemens AG of Germany.

SQUID magnetometers generally comprise a superconducting pick up coil system and a detector system (the SQUID) which itself comprises one or two Josephson junctions inserted into a loop of superconducting wire. The magnetic flux within such loops is quantized and changes in the magnetic field experienced by the pick up coils cause an immediate and measurable change in the current flowing through the detector. The SQUID magnetometers available include both single and multichannel devices, the latter being capable of detecting magnetic fields at plurality of locations simultaneously.

SQUID magnetometers are capable of measuring magnetic fields as low as $10^{-14}$ Tesla, one ten billionth the earth's magnetic field, and thus are able to detect magnetic fields generated by biological activity such as for example the fields of the order of $10^{-13}$T which are induced by the electrical activity of the brain. The sources of nerve signals can thus be traced to within a few millimeters.

SQUIDS and their use in the study of biomagnetism are discussed for example by Wolsky et al. Scientific American, February 1989, pages 60–69, Philo et al. Rev. Sci. Instrum. 48:1529–1536 (1977), Cohen IEEE Trans. Mag. MAG-11 (2):694–700 (1975), Farrell et al. Applied Physics Communications 1(1):1–7 (1981), Farrell et al. IEEE Trans. Mag. 16:818–823 (1980), and Brittenham et al. N. Eng. J. Med. 307(27):1671–1675 (1982). The SQUID may be designed to detect the magnetic field or, may be of the gradiometer type and which several designs exist.

Indeed the development of biomagnetic analysis has been closely linked to the development of SQUID detectors since conventional magnetometers, such as Barrington detectors or Hall-probe gaussmeters, are several orders of magnitude less sensitive to magnetic field changes.

In the study of biomagnetism, or more specifically, the in vivo measurement of magnetic susceptibility, the sensitivity of SQUIDS has been such that the researchers' concentration has primarily been on three areas—the detection of electrical activity within body tissues by detection of the accompanying magnetic field changes, the in vivo determination of iron concentrations in the liver in order to detect iron overload or iron deficiency there, and the detection of ferromagnetic particle contamination in the lungs.

In the first two cases, the magnetic fields detected by the SQUIDS arise from normal or stimulated nerve activity or from the normal presence of (paramagnetic) iron in the liver. In the third case, particle contamination is by magnetic particles, e.g. of magnetite, and their magnetic effect is first maximized by placing the subject in a magnetic field. The resultant magnetization is detectable by a SQUID for the period of months over which it decays.

Due to the extreme sensitivity of the SQUID technology enabling the body's electrical activity to be monitored, there has been little emphasis on the use of SQUIDS for the generation of images, in particular two or three dimensional images, of the body's internal physical structure rather than electrical activity images.

For such localisation to be effective it must be possible to generate magnetic susceptibility differences between different body tissues, organs and ducts and rather than doing this by provoking electrical activity or by relying on natural aggregations of non-diamagnetic material we now propose the administration in diagnostic magnetometery, especially magnetometric imaging, of enhancing agents comprising ferromagnetic or ferrimagnetic substances. SQUIDS are sufficiently sensitive to detect the changes in local magnetic susceptibility where such agents distribute within the body so enabling contrast enhanced magnetometric signals or images to be generated, for example for use in diagnostics.

SUMMARY OF THE INVENTION

Thus viewed from one aspect the present invention provides the use of a physiologically tolerable, particulate, free or matrix-borne, ferrimagnetic or ferromagnetic material for the manufacture of a diagnostic agent for administration into the gastrointestinal tract, the reproductive tract, the urinary tract, closed body cavities (e.g. into the synovial fluid or the vasculature), or the musculature for magnetometric imaging of the human or non-human, preferably mammalian, animal body.

Viewed from another aspect the invention also provides a method of generating a magnetometric image of the human or non-human animal body which method comprises administering into the gastrointestinal tract, the reproductive tract, the urinary tract, closed body cavities (e.g. into the synovial fluid or the vasculature) or the musculature of said body a physiologically tolerable particulate ferromagnetic or ferrimagnetic material and generating a magnetometric image of at least a part of said body into which said material distributes, in particular generating a two or three dimensional structural image and preferably but not essentially using a SQUID based imaging device, especially a multichannel SQUID imager.

Viewed from a still further aspect, the invention also provides a process for detecting variations in magnetic susceptibility within a human or non-human animal body which process comprises administering into the gastrointestinal tract, the reproductive tract, the urinary tract, closed body cavities (e.g. into the synovial fluid or the vasculature) or the musculature of said body a physiologically tolerable particulate ferromagnetic or ferrimagnetic material, and with a magnetometer continuously or repeatedly monitoring the magnetic susceptibility of at least a part of said body into which said material distributes whereby to generate magnetometric images of variations or abnormalities in blood flow, or to monitor the location and aggregation of these materials within regions of the body, for example the arrival and accumulation of tissue- or organ-targeting substances at the targeted region, e.g. a tumour, the reticuloendothelial system, etc. and generate a magnetometric image thereof.

Viewed from another aspect the invention also provides the use of a physiologically tolerable particulate ferromagnetic or ferrimagnetic material, and in particular free or matrix-borne, ferromagnetic or ferrimagnetic particles, for the manufacture of a diagnostic composition for use in the process according to the invention.

DETAILED DESCRIPTION OF THE INVENTION

Figure 1:
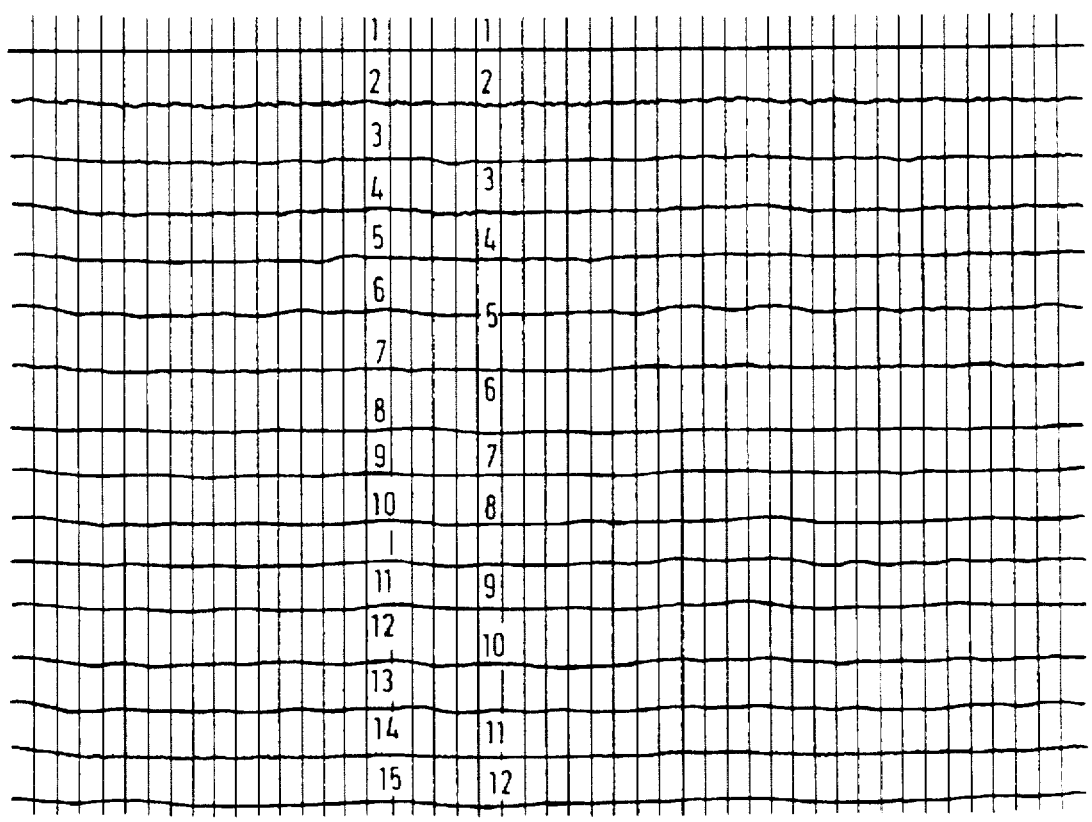
FIG. 1 shows SQUID signals without sample.

The method and process of the invention may be performed using any magnetometric technique but are particularly suited to the use of multichannel SQUID based magnetometers.

The ferrimagnetic or ferromagnetic substances used according to the invention and for convenience referred to herein as magnetometric diagnostic agents may, in view of the sensitivity of SQUID magnetometers, be any such material which is biotolerable in the dosages and with the administration form and route that is used. There is of course no necessity to pre-magnetize the subject following administration of the diagnostic agent before transferring the subject to the magnetometer location (generally a region of homogeneous magnetic field or a magnetically shielded room). However, the contrast agent may be pre-magnetised before administration and it may also be advantageous to protreat the magnetic substance to prevent conglomeration thus obtaining a maximum field for a given concentration of subtance.

The process and method of the invention can be performed with or without the imposition of an external magnetic field (besides or in place of the earth's natural magnetic field that is). Imposed fields can be variant, e.g. pulsed, or invariant. This field can be relatively localized in effect and can be as low as $10^{-4}$T but in one convenient embodiment may be the primary field, generally of up to $10^{1}$T, generated by the primary coils of a magnetic resonance imager.

Particular mention may be made of the ferromagnetic contrast agents already proposed for use as MRI contrast agents by for example Jacobsen et al. in U.S. Pat. No. 4,863,716.

The literature contains many suggestions for the formulation of paramagnetic particles and in particular suggests that the particles can be administered either free (i.e. uncoated and not bound to any other substance) or coated (e.g. dextran or lipid coated), or carried by or embedded in a matrix particle (e.g. a polysaccharide) or bound to an organ or tissue targetting molecule, e.g. a natural or synthetic biomolecule or derivative thereof such as an antibody, an antibody fragment, a protein or protein fragment, a hormone, a lectin, lymphokine, a growth factor, ferritin or a nerve adhesion molecule (see for example WO-A-92/04916).

Where the coating is a biologically relatively inert material such as a polysaccharide (e.g. dextran), a naturally occurring protein or a lipid it is preferred that the coating give the particle an overall charge, preferably a negative charge.

Due to the sensitivity of SQUIDS, which should be able to detect very small numbers of or even single magnetic crystal loaded matrix particles, tumour or other disease imaging or localization using ferri- or ferromagnetic particles linked to a targetting molecule, e.g. an antibody, may be of significant practical interest.

For such tumour or disease imaging or localization, one may conveniently use magnetic crystal loaded matrix particles where the matrix is coupled to a targetting molecule, or coated, e.g. silanized, magnetic crystals where the coating is coupled to a targetting molecule.

Parenterally administrable particulate magnetometric diagnostic (MD) agents are also of particular interest in the imaging of the liver, spleen and lymphatic due to the action of the reticuloendothelial system (RES) in removing such particles from the blood stream. For lymphatic imaging, dextran or polyethylene glycol coatings, or other agents reducing RES uptake, may be especially preferred. The MD agents can, as mentioned above also be administered into other closed body cavities, such as the joints, e.g. the knee. However MD agents and especially particulate agents may also be used to advantage in the magnetometric diagnosis or imaging of body ducts and cavities having external voidance ducts, e.g. the gastrointestinal tract, the bladder and the uterus, where the MD agent can be administered orally, rectally or through a catheter into the body cavity of interest.

For axonal imaging, lymphatic system imaging or synovial fluid imaging by magnetometry, one may use superparamagnetic and paramagnetic materials coated or labelled as discussed above and the use of paramagnetic, superparamagnetic, ferromagnetic and ferrimagnetic materials for the manufacture of contrast agents for magnetometric axonal imaging or magnetometric lymph node imaging form a further aspect of the invention. Appropriate superaparamagnetic and paramagnetic materials are discussed in WO-A-91/15243.

Many different ways of achieving tissue, organ, and disease specificity for soluble and particulate diagnostic agents are already known.

Thus by attachment to fatty acids and other substances with a specific hydrophilic/hydrophobic ratio the agent will after intravenous injection efficiently accumulate in the hepatocytes. Hepatocytes also have specific lectins and sugar moieties present on their surface. The latter causes specific oligosaccharides, glycoproteins and lectins to accumulate in the hepatocyte compartment of the liver. The Kupffer cells as well as the endothelial cells of the liver also possess unique receptors (e.g. lectins) on their surface, causing other types of ligands (e.g. glycoproteins) to accumulate in these compartments. The endothelial cells of the liver have receptors for specific molecules such as hyaluronic acid, enabling other types of targeting vehicles also to be used for this compartment.

It is possible to bind the MD agent to monoclonal antibodies specific for almost any macromolecular structure. Different organs have cells containing organ-specific structures on their surface. Using monoclonal antibodies (or derivatives or fragments thereof) reacting with organ-specific structure, it is thus possible to produce organ-specific vehicles.

Furthermore, hormones, growth factors and lymphokines often have organ-specific receptors. Consequently, "natural"

human proteins of this type or their mimetics may also be used as targeting vehicles.

The production of antibody coupled particles suitable for use in the invention is described by Renshaw et al. in Magnetic Resonance Imaging 4:351–357 (1986).

These types of targeting vehicles will cause accumulation in normal organs, and if these are deformed and non-homogeneous due to disease, MD agents attached to such vehicles will provide important diagnostic information. However, for direct disease visualization, targeting vehicles with affinity for disease-specific structures should be employed.

Thus pathologically altered cells (e.g. tumour cells) possess unique surface markers, and monoclonal antibodies reacting with a number of such structures have been developed. Pathology-specific monoclonal antibodies coupled to MD agents can thus be used to obtain disease information, e.g. by visualization.

Thrombi contain a number of specific structures, for instance fibrin. Consequently, MD agents coupled to fibrin-specific antibodies will after intravenous injection accumulate in the clots, and can be used for localization of the thrombi.

In the same way as Mabs with affinity for clots can be developed, the naturally occurring protein tPA and the anticoagulant peptide hyrudin have affinity for fibrin. tPA or hyrudin coupled MD agents would thus accumulate in thrombi and be useful for their detection.

Upon cell necrosis, intracellular structures like myosin, histones and actin are exposed to macromolecules normally confined to the extracellular space. Coupled to MD agents Mabs against both the above structures may thus be used to visualise infarcts/necrosis.

Where magnetic particle containing contrast media are administered parenterally, and especially intravascularly, the biodegradation and ultimate excretion of the particle metabolites may be enhanced by formulating the particles together with a chelating agent as described in WO-A-89/11873.

The ferri- or ferromagnetic particles themselves may be of any material which, although preferably non-radioactive (unless the particles are also intended to be detected by their radioactive decay emissions), exhibits ferri- or ferromagnetism in domain and sub-domain sized crystals. Conveniently the particles will be of a magnetic metal or alloy, e.g. of pure iron, but more preferably they will be of a magnetic iron oxide, e.g. magnetite, or a ferrite such as cobalt, nickel or manganese ferrites.

The magnetic particles useful according to the invention will preferably have average overall particle sizes up to 10 µm, especially up to 1 µm. Generally, however the particle sizes for individual magnetic crystals will preferably up to 1 µm, especially up to 400 nm. For administration into the systemic vasculature or the musculature the overall particle size will particularly preferably be up to 800 nm, especially up to 500 nm. For administration into the GI tract or the reproductive or urinary tracts overall particle size will preferably be up to millimeter size, e.g. 100 nm–5 µm, especially 200 nm–3 µm. The magnetic crystals of course will be at least single domain size. Generally this is of the order of 100 nm.

The dosages of the MD agent used according to the method of the present invention will vary according to the precise nature of the MD agent used, of the magnetometer being used and of the tissue or organ of interest. Preferably however the dosage should be kept as low as possible while still achieving a detectable variation in magnetic susceptibility.

In general, the MD agents used according to the invention should be administered in a quantity sufficient to produce a concentration, expressed in terms of susceptibility of at least $10^{-9}$ emu/g, preferably at least $5 \times 10^{-9}$ emu/g, especially at least $10^{-8}$ emu/g.

Thus viewed from a further aspect the invention provides a magnetic susceptibility MD medium in aqueous form containing a physiologically tolerable ferrimagnetic or ferromagnetic substance together with at least one pharmaceutical carrier or excipient, the magnetic susceptibility of said medium (at STP) being in the range $10^{-12}$ to $10^{-6}$, preferably $10^{-11}$ to $2 \times 10^{-7}$, especially preferably $10^{-10}$ to $5 \times 10^{-8}$, in particular $10^{-9}$ to $10^{-8}$, emu/g.

Alternatively expressed, for most magnetic materials the novel MD media will conveniently contain the magnetic metal at a concentration of at least $10^{-14}$M, generally at least $10^{-10}$M, preferably at least $10^{-8}$M, in particular at least 0.05 mM, especially at least 0.2 mM, more preferably at least 0.3 mM, most preferably at least 1.0 mM, e.g. 0.0002 to 2M, more especially 0.0003 to 1.5M.

The MD media of the invention may contain particularly low concentrations of the contrast agent where it is a highly specifically targeted material. Thus for an agent specific for small tumours minimum dosages of the order of $10^{-14}$M/Kg may be adequate, for liver specific agents minimum dosages may be of the order of $10^{-11}$M/Kg and for agents which distribute broadly within the body minimum dosages of $10^{-10}$M/kg may be appropriate. These will generally be administered in volumes of 0.1 ml to 1000 ml. The upper limit for MD agent dosages will be generally comparable to that for MRI contrast agents and may be dictated by toxicity constraints.

For most MD agents the appropriate dosage will generally lie in the range 0.02 µmol to 3 mmol paramagnetic metal/kg bodyweight, especially 1 µmol to 1.5 mmol/kg, particularly 0.01 to 0.5, and more especially 0.1 to 0.4 mmol/kg.

Where less sensitive non-SQUID magnetometers are used according to the invention, the MD agent concentrations required will of course be higher than are needed using SQUID magnetometers.

It is well within the skill of the average practitioner in this field to determine the optimum dosage for any particular MD agent by simple experiment, either in vivo or in vitro.

MD agents may be formulated with conventional pharmaceutical or veterinary aids, for example, stabilizers, antioxidants, osmolality adjusting agents, buffers, pH adjusting agents, etc., and may be in a form suitable for enteral or parenteral administration, e.g. oral, rectal, intravascular etc. Particularly preferably the MD agents will be in forms suitable for ingestion, injection or infusion directly or after dispersion in or dilution with a physiologically acceptable carrier medium, e.g. water for injections. Thus the contrast agents may be formulated in conventional administration forms such as powders, solutions, suspensions, dispersions etc., however solutions, suspensions and dispersions in physiologically acceptable carrier media will generally be preferred.

The MD agents may therefore be formulated for administration using physiologically acceptable carriers or excipients in a manner fully within the skill of the art. For example, the MD agents optionally with the addition of pharmaceutically acceptable excipients, may be suspended or dissolved in an aqueous medium, with the resulting solution or suspension then being sterilized. Suitable additives include, for example, physiologically biocompatible buffers chelating agents (as for example DTPA or DTPA-bisamide (e.g. 6-carboxymethyl-3,9-bis(methylcarbamoyl methyl)-3,6,9-triazaundecanedioic acid)) or calcium chelate complexes (as for example salt forms of the calcium DTPA complex or the calcium DTPA-bisamide complex, such as NaCaDTPA-bisamide) or, optionally, additions.(e.g. 1 to 50 mole percent) of calcium or sodium salts (for example, calcium chlorie, calcium ascorbate, calcium gluconate or calcium lactate and the like).

Parenterally administerable forms, e.g., intravenous solutions, should of course be sterile and free from physiologically unacceptable agents, and should not have too high or too low an osmolality so as to minimize irritation or other adverse effects upon administration and thus the MD medium should preferably be isotonic or slightly hypotonic or hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the MD agents and which will not interfere with the manufacture, storage or use of the products.

It will be realized of course that since the MRI contrast media can be used as MD media it will be particularly convenient to investigate the subject using MRI to supplement or confirm diagnostic information derived from the magnetometer investigations. Moreover, images from MRI or other conventional imaging modalities may be used to provide a "native" image onto which the magnetometric information or image may be superimposed—this is of particular value where the biodistribution of the magnetometric contrast agent is very specific. Similarly the magnetometric investigation technique of the invention may be used to investigate the distribution of materials administered as MRI contrast agents, particularly preferably using relatively inexpensive non-SQUID magnetometers.

Accordingly, viewed from a still further aspect the invention provides a magnetic resonance imaging apparatus, characterized in that it is provided with magnetometric detection means. In this way the invention provides a magnetometer adapted for the detection of magnetic resonance imaging contrast agents within a human or non human animal subject and preferably also for the generation of a magnetometric image of said subject, i.e. being a combination of a magnetometer and MRI imager. Such a combined magnetometer/MRI imager may be produced by straightforward modification of existing MRI apparatus to incorporate suitable magnetometric detector means. Thus for example a Hall probe on an array of such probes may be so mounted in an MRI imager as to allow a body within such an imager to be scanned eg. by rotation of the probe or probe array about the axis of said imager, as to allow a magnetometric image to be generated. Alternatively a static array of Hall probes may be disposed about the imaging cavity of the MRI imager so allowing a magnetometric image to be generated without requiring physical displacement of the Hall probes. In either event the operation of the Hall probes and the magnetometric image generation may conveniently be controlled by the same computer as controls its MRI imaging operations.

The invention will now be illustrated further with reference to the following non-limiting Examples.

EXAMPLE 1

Oral ferromagnetic MD agent for abdominal studies

| Microcrystalline cellulose | 2300 g |
| Xanthan gum | 400 g |
| Corn starch | 1400 g |
| Aspartame | 15 g |

The substances are dry blended and granulated with a granulating liquid of the following composition:

| Polyvinyl pyrrolidone | 200 g |
| Iron fine powder (Riedel-deHaën no. 12310) | 5 g |
| Purified water | 1800 g |

The granulated is dried and screened to give a granulate fraction of 0.3 to 1.5 mm. Before administration 10 g of the granulate suspended in 100 ml water will give a viscosity of approximately 2500 cps when fully hydrated. For at least three-minutes from suspension the viscosity remains sufficiently low (less than about 200 cps) for easy administration, e.g. by ingestion.

EXAMPLE 2

Oral ferromagnetic MD agent for abdominal studies

| Iron (II,III)-oxide black magnetic (Kock-Light Limited), Haverhill, Suffolk, England | 0.5 g |
| Hydroxyethyl cellulose | 10.0 g |
| Methyl parahydroxybenzoate | 0.3 g |
| Propyl parahydroxybenzoate | 0.2 g |
| Ethanol | 10.0 g |
| Mannitol | 15.0 g |
| Saccharin sodium | 1.0 g |
| Orange essence | 0.3 g |
| Apricot essence | 0.7 g |
| Water | 952.0 g |

The hydroxyethyl cellulose was dispersed in water with stirring for 2 hours. Saccharin sodium, mannitol and a solution of the essences, and methyl and propyl parahydroxybenzoate in ethanol were slowly added. The magnetic particles were dispersed in the solution under vigorous stirring. The suspension contained 0.05 mg Fe/g.

EXAMPLES 3-4

Multi-channel SQUID analysis of 0.5% agar gels containing MD agents.

SQUID Instrument: Krenikon (SIMENS AG)

All samples were moved with the same frequency (appr. 4 Hz) during the experiments.

SQUID signals (16 channels) without sample is shown in FIG. 1.

EXAMPLE 3

MD agent: Black iron oxide particles from Anstead Ltd., England

Concentration: 0.1 mmol/kg

Distance from detector: 5 cm

Figure 2:
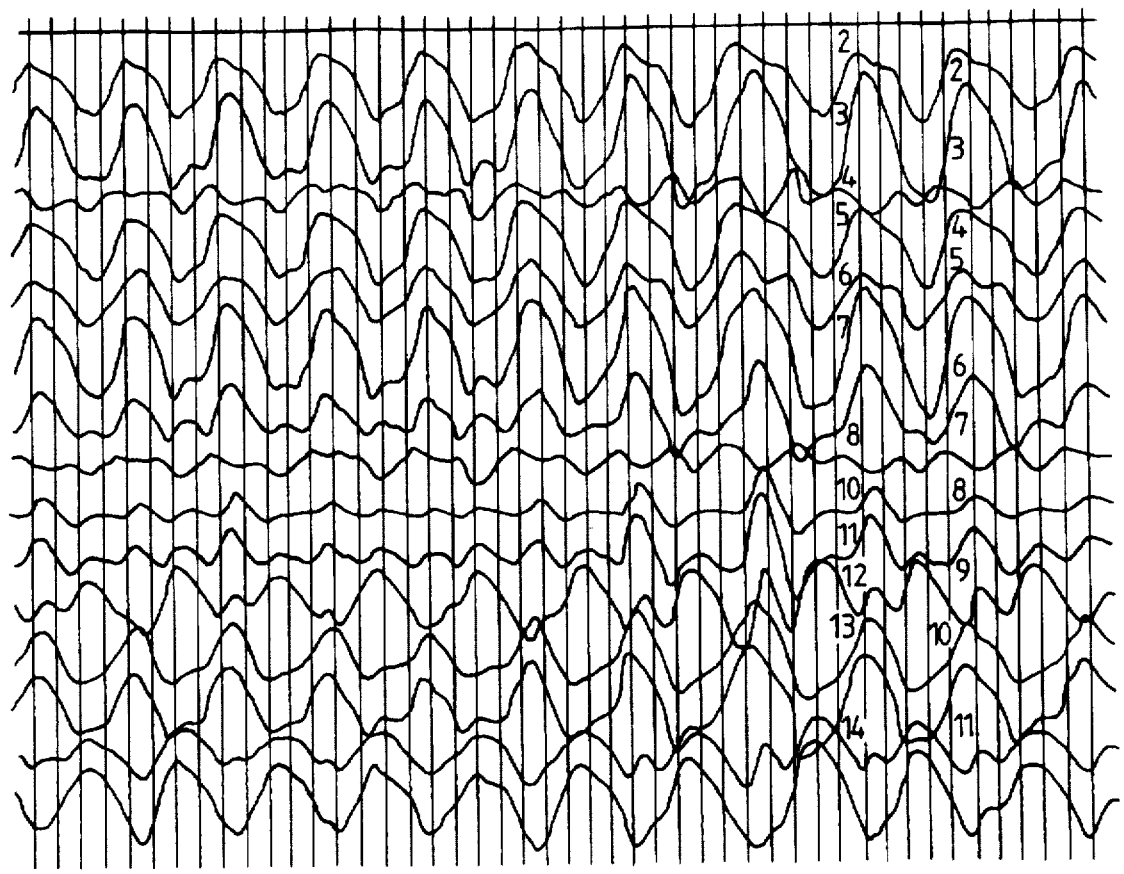
FIG. 2 shows SQUID signal of black iron oxide particles (0.1 mmol/kg)

Results shown in FIG. 2.

EXAMPLE 4

MD agent: Black iron oxide particles from Anstead Ltd., England

Figure 3:
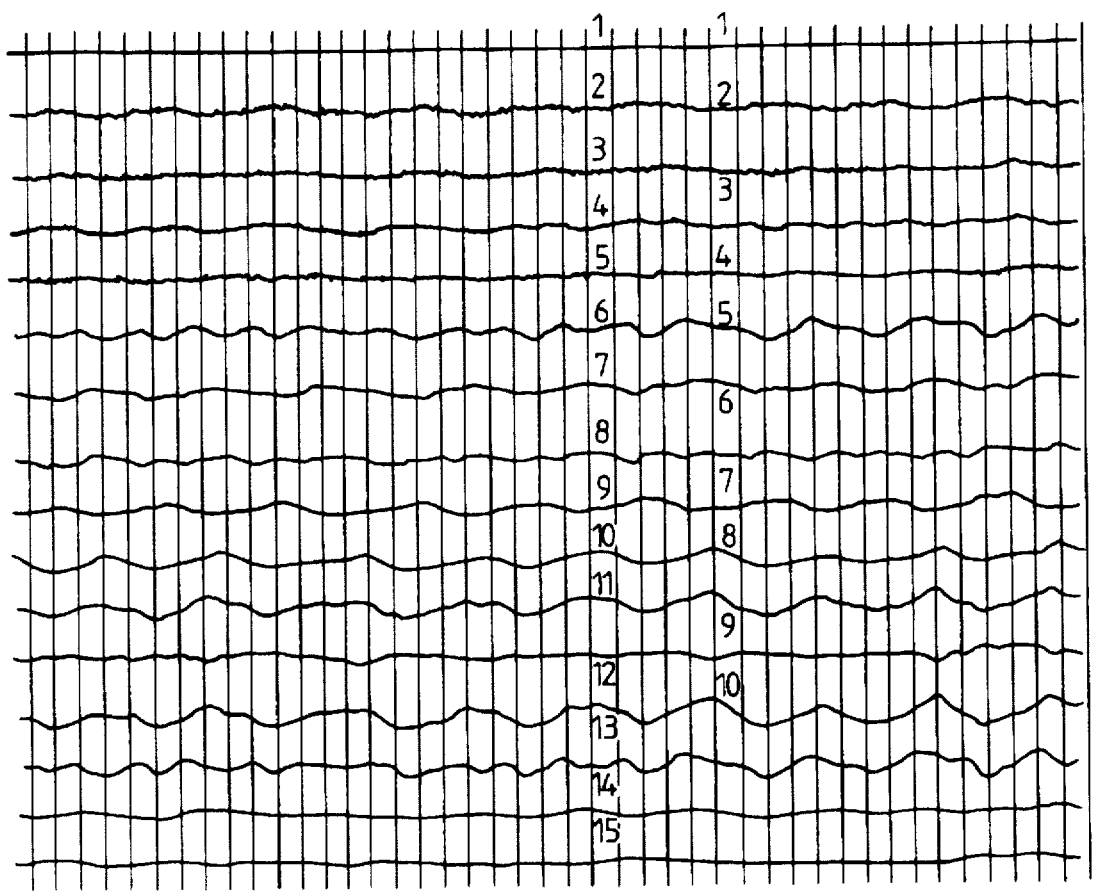
FIG. 3 shows SQUID signal of black iron oxide particles (0.0001 mmol/kg).

Concentration: 0.0001 mmol/kg
   Distance from detector: 1 cm.
   Results shown in FIG. 3.

EXAMPLES 5–6

Multi-channel SQUID analysis of the same samples as described in Example 3–4 after magnetization of the samples with a small, strong (about 0.3 T) permanent magnet showed enhanced magnetometric effect compared to the non-magetized samples.

(No corrections have been made for potential magnetization of the empty plastic test tubes).

EXAMPLES 7–8

SQUID analyses of the samples in Examples 3–6 are performed on an instrument detecting magnetic fields. Enhanced efficiency is observed.

(The instrument used in Examples 5–6 detects magnetic field gradients and not the absolute magnetic fields).

EXAMPLES 8–9

Low concentration intravenous MD media

The MD media of Examples 1 and 2 are diluted, 1 part by volume with 99 parts by volume of water for injections to produce more dilute contrast media suitable for use with sensitive SQUID based magnetometers.

Still lower concentrations, e.g. at the $10^{-10}$–$10^{-6}$M level, can be produced by further dilution.

We claim:

1. A method of generating a magnetometric image of a human or non-human animal body which method comprises administering into the gastrointestinal tract, the reproductive tract, the urinary tract, a closed body cavity or the musculature of said body physiologically tolerable lipid-coated ferromagnetic or ferrimagnetic particles and generating a magnetometric image of at least a part of said body into which said particles distribute.

2. A method as claimed in claim 1 wherein said step of generating a magnetometric image comprises detecting magnetic field perturbations within said body using a SQUID-based magnetometer and generating a two- or three-dimensional image of said body.

3. A method as claimed in claim 2 wherein in an additional step a magnetic resonance image of said body is generated as a reference image.

4. A method as claimed in claim 1 wherein in an additional step a magnetic resonance image of said body is generated as a reference image.

5. A method of generating a magnetometric image of a lymph node of a human or non-human animal body which method comprises administering into the lymph node physiologically tolerable dextran-coated paramagnetic, ferromagnetic or ferrimagnetic particles and generating a magnetometric image of said lymph node.

6. A method as claimed in claim 5 wherein said step of generating a magnetometric image comprises detecting magnetic field perturbations within said lymph nodes using a SQUID-based magnetometer and generating a two- or three-dimensional image of said lymph node.

7. A method as claimed in claim 6 wherein in an additional step a magnetic resonance image of said lymph node is generated as a reference image.

8. A method as claimed in claim 5 wherein in an additional step a magnetic resonance image of said lymph node is generated as a reference image.

9. A method of generating a magnetometric image of an axonal system of a human or non-human animal body which method comprises administering into the axonal system physiologically tolerable nerve-adhesion molecule-labelled paramagnetic, ferromagnetic or ferrimagnetic particles and generating a magnetometric image of said axonal system.

10. A method as claimed in claim 9 wherein said step of generating a magnetometric image comprises detecting magnetic field perturbations within said axonal system using a SQUID-based magnetometer and generating a two- or three-dimensional image of said axonal system.

11. A method as claimed in claim 10 wherein in an additional step a magnetic resonance image of said axonal system is generated as a reference image.

12. A method as claimed in claim 9 wherein in an additional step a magnetic resonance image of said axonal system is generated as a reference image.

* * * * *